US00PP20605P2

(12) United States Plant Patent
Elsley

(10) Patent No.: US PP20,605 P2
(45) Date of Patent: Dec. 22, 2009

(54) ***LIRIOPE* PLANT NAMED 'SNO CONE'**

(50) Latin Name: *Liriope muscari*
Varietal Denomination: Sno Cone

(75) Inventor: John E. Elsley, Greenwood, SC (US)

(73) Assignee: Itsaul Plants, LLC., Alpharetta, GA (US)

( * ) Notice: Subject to any disclaimer, the term of this patent is extended or adjusted under 35 U.S.C. 154(b) by 0 days.

(21) Appl. No.: 12/288,773

(22) Filed: Oct. 23, 2008

(51) Int. Cl.
*A01H 5/00* (2006.01)

(52) U.S. Cl. ..... Plt./450
(58) Field of Classification Search ..... Plt./450
See application file for complete search history.

*Primary Examiner*—June Hwu
(74) *Attorney, Agent, or Firm*—Penny J. Aguirre

(57) ABSTRACT

A new cultivar of *Liriope*, 'Sno Cone', characterized by its tight clump-forming and non-spreading growth habit, its strongly recurved foliage that is green and white foliage with the white coloration increasing with leaf maturation and retained throughout the growing season, and its uniquely colored berries in fall that are mottled with purple, green, and white.

2 Drawing Sheets

Botanical classification: *Liriope muscari.*
Varietal denomination: 'Sno Cone'.

BACKGROUND OF THE INVENTION

The present invention relates to a new and distinct cultivar of *Liriope muscari* and will be referred to hereafter by its cultivar name, 'Sno Cone'. 'Sno Cone' is a new cultivar of lilyturf or border grass and is a grass-like perennial herb in the Lily family grown for landscape and container use.

The Inventor discovered 'Sno Cone' as a naturally occurring whole plant mutation of *Liriope muscari* in summer of 1988 in his garden in Greenwood, S.C. The parentage of 'Sno Cone' is unknown.

Asexual reproduction of the new cultivar was first accomplished by division under the direction of the Inventor in Dahlonega, Ga. in summer of 2004. The characteristics of this cultivar have been determined both by division and in vitro propagation to be stable and to reproduce true to type in successive generations.

SUMMARY OF THE INVENTION

The following traits have been repeatedly observed and represent the characteristics of the new cultivar. The new *Liriope* has not been observed under all possible environmental conditions. The phenotype may vary somewhat with variations in temperature, day-length, light intensity, soil types, and water and fertility levels without, however, any variance in genotype. The general observations, and descriptions that follow describe plants that have been observed over a period of ten years in Greenwood, S.C. These attributes in combination distinguish 'Sno Cone' from all other selections of *Liriope* known to the Inventor.

1. 'Sno Cone' exhibits a tight clump forming, non-spreading growth habit.
2. 'Sno Cone' exhibits foliage that emerges greenish-white in color and becomes whiter in color with maturity, the white coloration is maintained throughout the growing season.
3. 'Sno Cone' exhibits foliage that is strongly recurved.

4. 'Sno Cone' exhibits ornamental berries in fall that are uniquely colored with a mottled pattern of dark purple, green, and white.
5. 'Sno Cone' reaches a height of 30 to 40 cm (12 to 16 inches).

'Sno Cone' can be compared to the cultivar 'Okino' (not patented), which is similar in having white and green foliage, 'Sno Cone' differs from 'Okino' in being taller, in having a more vigorous growth habit, and in having foliage that is more recurved, broader in width, and that maintains its white coloration throughout the growth season. 'Sno Cone' can also be compared to the cultivar 'Big Blue' (not patented), which is similar in having a tight clumping habit. 'Sno Cone' differs from 'Big Blue' in having foliage that is more recurved and in having white and green foliage whereas 'Big Blue' exhibits blue-green foliage.

BRIEF DESCRIPTION OF THE DRAWING

The accompanying colored photographs illustrate the overall appearance and distinct characteristics of the new *Liriope*. The photographs in FIG. 1 and FIG. 2 were taken of 4 year-old plants as grown in a garden in Atlanta, Ga.

The photograph in FIG. 1 illustrates the overall habit and appearance of a group of plants of 'Sno Cone' in bloom in mid summer.

Figure 1:
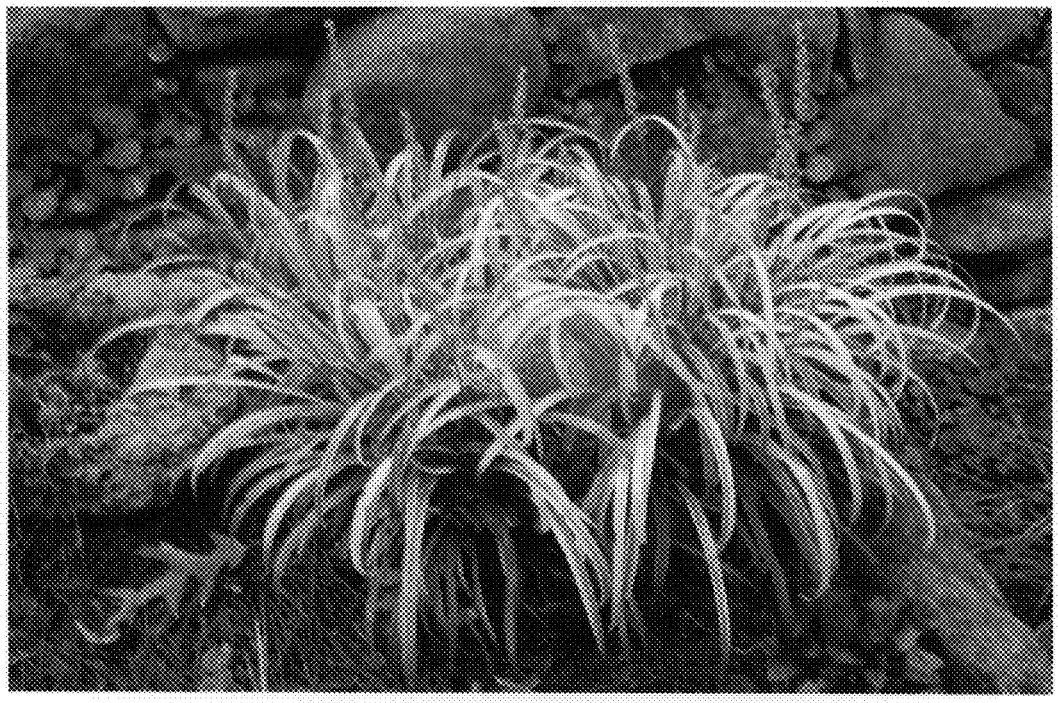
Figure 2:
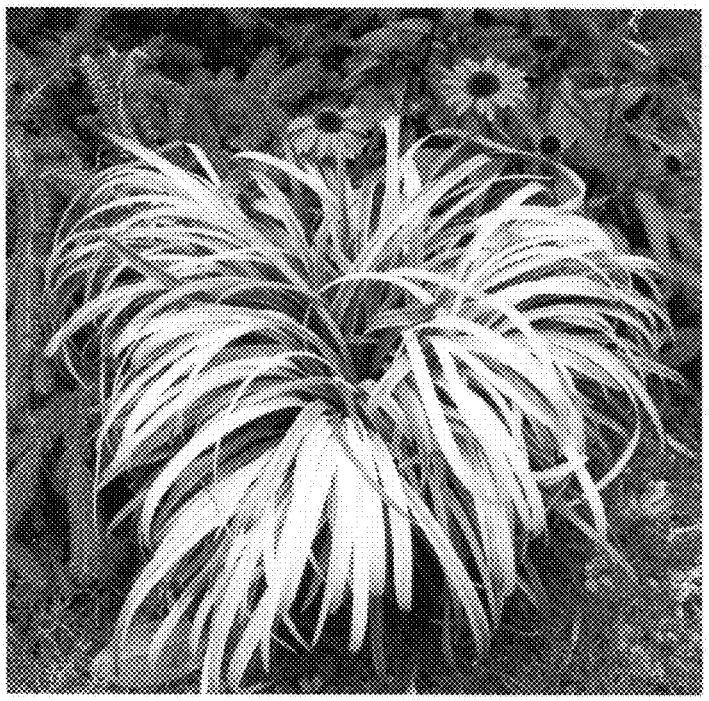

The photograph in FIG. 2 was taken of a single plant of 'Sno Cone' in late summer and illustrates the whitening of the foliage later in the season.

Figure 3:
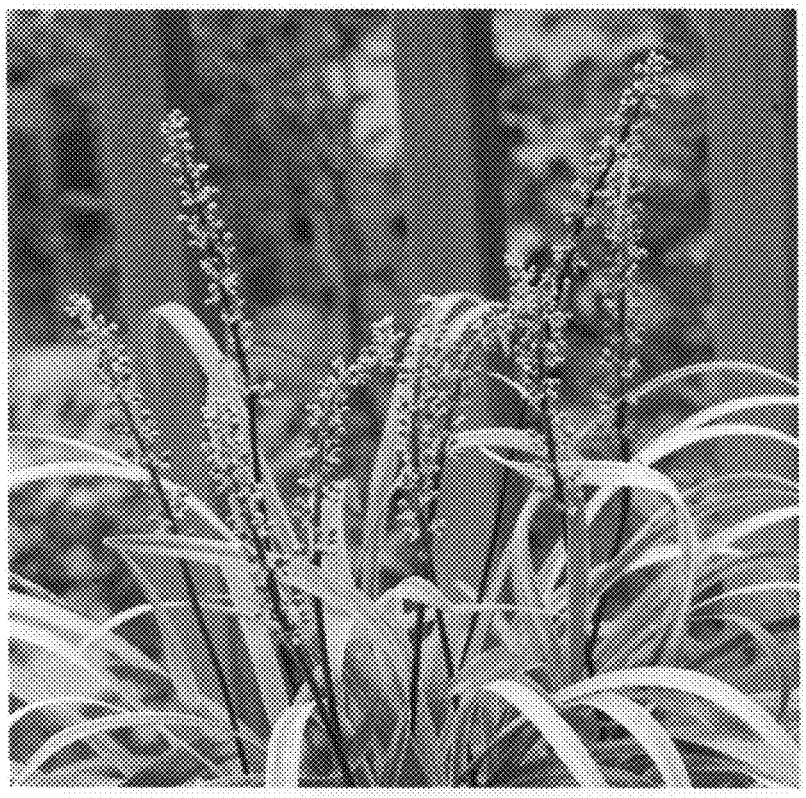

The photograph in FIG. 3 was taken of a one-year-old plant of 'Sno Cone' as grown in a one-gallon container in Alpharetta, Ga. and provides a close-up view of the inflorescences.

Figure 4:
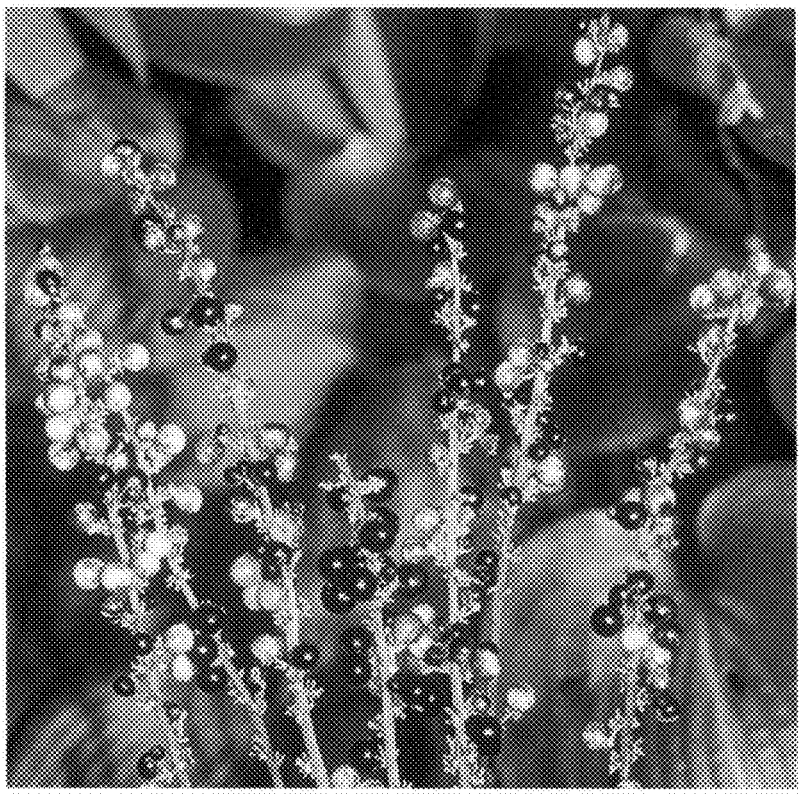

The photograph in FIG. 4 was taken of the original plant in Greenwood, S.C. and presents a view of the berries of 'Sno Cone'.

The colors in the photograph may differ slightly from the color values cited in the detailed botanical description, which accurately describe the colors of the new *Liriope*.

DETAILED BOTANICAL DESCRIPTION

The general observations describe plants of 'Sno Cone' that were observed for 20years in a garden in Greenwood, S.C., while the detailed botanical data describe one year-old plants as grown in one-gallon containers in Alpharetta, Ga. The color determinations are in accordance with the 2007 R.H.S. Colour Chart of The Royal Horticultural Society, London, England, except where general color terms of ordinary dictionary significance are used.

General description:

*Blooming habit*.—From June to early September in Southeastern U.S.A.

*Plant habit*.—Herbaceous, perennial herb with a tightly clump forming habit of tufted, recurved, and evergreen foliage.

*Height and spread*.—About 40 cm (16 inches) in height in bloom with foliage about 30 cm (12 inches) in height and reaches a spread of 91 cm (3 ft) in 20 years.

*Hardiness*.—U.S.D.A. Zones 6 to 10.

*Diseases and pests*.—No unique aspects concerning susceptibility or resistance to diseases or pests has been observed.

*Root description*.—Fleshy.

*Branching*.—Stem-less, tufted shoots arise from base.

Growth and propagation:

*Propagation*.—Tissue culture or division.

*Time required for root development*.—Roots appear in tissue culture in 14 days when grown at 73° F. under 16 hours of light per day, plantlets are ready to transplant after 28 days after transfer to rooting medium, by division; a one-gallon plant will root in a one-gallon container in about 8 weeks.

*Growth rate*.—Moderately vigorous.

Foliage description:

*Leaf shape*.—Linear.

*Leaf division*.—Simple.

*Leaf base*.—Truncate to rootstock.

*Leaf apex*.—Narrowly acute.

*Leaf aspect*.—Leaves initially emerge upright, then arch and curl when mature.

*Leaf venation*.—Parallel, the midrib is raised on the lower surface, not prominent or conspicuous, color matches leaf color.

*Leaf margins*.—Entire.

*Leaf attachment and arrangement*.—Sessile, arise in tufts from rootstock.

*Leaf size*.—Average of 1 cm in width (at midpoint) and up to about 38 cm in length.

*Leaf number*.—Average of 25 per rootstock (shoot) with average of 15 shoots per one-gallon plant.

*Leaf surface*.—Glabrous on upper and lower surface.

*Leaf color and variegation pattern*.—Basic variegation pattern on emerging and mature foliage consists of stripes and mottling of various shades of green and white, similar pattern and coloration exists on both the upper and lower surfaces: mottling and stripes of 157A to 157C, 137A to 137D, and 147A, with base of leaves more solid; 137C becoming 159A at point of attachment, young leaves and mature leaves have similar coloration, however leaves become predominantly more white (157A to 157C) as the leaves mature.

Flower description:

*Inflorescence type*.—An upright held raceme comprised of corymb-like tufts of campanulate flowers arranged in whorls on the upper portion of the scape.

*Inflorescence size*.—Reaches up to 10 cm in height and about 1.7 cm in width.

*Flower fragrance*.—None.

*Flower quantity*.—Average of 12 flowering stems per plant well developed in a one-gallon container in mid July, average of 125 flowers per scape, arranged in about 25 tufts of about 5 flowers each.

*Flower lastingness*.—Flowers open the entire length of the scape, with corymb-like tufts opening sequentially, average of 14 days per flower, with raceme blooming for about 3 weeks.

*Flower buds*.—Oblong-globose in shape, average of 2 mm in diameter and 3 mm in length, a blend of 79C and 79D in color.

*Flower aspect*.—Held horizontally to about 45° angle from scape.

*Flower shape*.—Campanulate.

*Flower size*.—About 4 mm in depth and 3 mm in diameter.

*Tepals*.—About 6, ovate in shape, margin is entire, apex is broadly acute, upper and lower surface is glabrous and waxy, color is a blend of 79C and 79D on both surfaces, about 4 mm in length and 2 mm in width.

*Peduncles*.—About 32 cm in length (from base of plant to top of raceme) and an average of 3 mm in width, held erect, strong, color is a blend of 147A and N186A below raceme and raceme portion is N77B, surface is slightly pubescent.

*Pedicels*.—Average of 2.5 mm in length and 1 mm in width, N77D in color, surface is glabrous.

Reproductive organs:

*Gynoecium*.—1 Pistil, club-shaped, about 2.5 mm in length and 1.5 mm in width, stigma is 91D in color, style is continuous with superior ovary and is about 2 mm in length and 1.5 mm in width and 79D in color.

*Androcoecium*.—6 stamens, anthers are held upright and pointed, basifixed, about 1.5 mm in length and 1 mm width and 7C in color, filaments are about 1 mm in length and 91D in color, pollen was not discernable.

*Fruit and seed*.—Berries; present for about 3 weeks in fall, globose in shape, an average of 8 mm in diameter, mottled in color with 155C, 144A to 144B, 137A, and a color between 203A and N92C and a blending of the aforementioned colors, seed; 1 per berry, round in shape, an average of 7 mm in diameter, fleshy, 162D in color.

It is claimed:

1. A new and distinct cultivar of *Liriope* plant named 'Sno Cone' as herein illustrated and described.

* * * * *